United States Patent
Urbanski et al.

(10) Patent No.: US 9,005,138 B2
(45) Date of Patent: Apr. 14, 2015

(54) WIRE GUIDE HAVING DISTAL COUPLING TIP

(75) Inventors: Jason Urbanski, Ellettsville, IN (US); Jeffry S. Melsheimer, Springville, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 2212 days.

(21) Appl. No.: 11/507,993

(22) Filed: Aug. 22, 2006

(65) Prior Publication Data
US 2007/0185414 A1    Aug. 9, 2007

Related U.S. Application Data

(60) Provisional application No. 60/711,102, filed on Aug. 25, 2005.

(51) Int. Cl.
A61M 25/09    (2006.01)
A61M 25/00    (2006.01)
A61M 25/01    (2006.01)

(52) U.S. Cl.
CPC .......... *A61M 25/09* (2013.01); *A61M 25/0045* (2013.01); *A61M 25/0068* (2013.01); *A61M 25/0069* (2013.01); *A61M 25/007* (2013.01); *A61M 2025/018* (2013.01); *A61M 2025/09083* (2013.01)

(58) Field of Classification Search
CPC ............ A61M 25/09; A61M 25/0068; A61M 2025/09183; A61M 2025/0183
USPC .......... 600/585, 434, 564; 604/531, 530, 528, 604/526, 535, 103.04; 607/122
See application file for complete search history.

(56) References Cited

U.S. PATENT DOCUMENTS

| 2,657,691 A | 11/1953 | Nordstrom, Jr. |
| 3,521,620 A | 7/1970 | Cook |
| 3,547,103 A | 12/1970 | Cook |
| 3,656,680 A | 4/1972 | Nomura |
| 3,739,784 A | 6/1973 | Itoh |

(Continued)

FOREIGN PATENT DOCUMENTS

| EP | 0 436 303 A1 | 11/1990 |
| EP | 0 829 269 A1 | 3/1998 |

(Continued)

OTHER PUBLICATIONS

International Search Report & Written Opinion (Jan. 3, 2008).

(Continued)

*Primary Examiner* — Adam Eiseman
(74) *Attorney, Agent, or Firm* — Brinks Gilson & Lione

(57) ABSTRACT

A coupling wire guide for intracorporeal procedures that may be coupled to a previously introduced wire guide, thereby permitting introduction of the coupling wire guide separately and identically in a manner that is both reliable as well as traceable. One embodiment of the wire guide includes a main body having a distal end and a tip portion connected to the distal end of the main body. The tip portion defines an axial passageway having a distal opening and a proximal opening, the passageway being sized to receive a second wire guide therein. The tip portion includes a linking member connected to the distal end of the main body to provide a secure connection between the distal end of the main body and the tip portion.

28 Claims, 3 Drawing Sheets

(56) References Cited

U.S. PATENT DOCUMENTS

| | | |
|---|---|---|
| 3,890,977 A | 6/1975 | Wilson |
| 4,548,206 A | 10/1985 | Osborne |
| 4,569,347 A | 2/1986 | Frisbie |
| 4,601,713 A | 7/1986 | Fuqua |
| 4,650,472 A | 3/1987 | Bates |
| 4,665,906 A | 5/1987 | Jervis |
| 4,824,435 A | 4/1989 | Giesy et al. |
| 4,921,483 A | 5/1990 | Wijay et al. |
| 4,925,445 A | 5/1990 | Sakamoto et al. |
| 4,934,380 A | 6/1990 | De Toledo |
| 4,984,581 A | 1/1991 | Stice |
| 5,003,990 A | 4/1991 | Osypka |
| 5,046,497 A | 9/1991 | Millar |
| 5,069,226 A | 12/1991 | Yamauchi et al. |
| 5,105,818 A | 4/1992 | Christian et al. |
| 5,129,890 A | 7/1992 | Bates et al. |
| 5,131,407 A | 7/1992 | Ischinger et al. |
| 5,159,861 A | 11/1992 | Anderson |
| 5,213,111 A | 5/1993 | Cook et al. |
| 5,234,003 A | 8/1993 | Hall |
| 5,242,759 A | 9/1993 | Hall |
| 5,243,996 A | 9/1993 | Hall |
| 5,251,640 A | 10/1993 | Osborne |
| 5,267,958 A | 12/1993 | Buchbinder et al. |
| 5,306,261 A | 4/1994 | Alliger et al. |
| 5,318,527 A | 6/1994 | Hyde et al. |
| 5,325,746 A | 7/1994 | Anderson |
| 5,328,472 A | 7/1994 | Steinke et al. |
| 5,328,480 A | 7/1994 | Milker et al. |
| 5,344,413 A | 9/1994 | Allman et al. |
| 5,354,257 A | 10/1994 | Roubin et al. |
| 5,383,853 A | 1/1995 | Jung et al. |
| 5,402,799 A | 4/1995 | Colon et al. |
| 5,449,362 A | 9/1995 | Chaisson et al. |
| 5,456,680 A | 10/1995 | Taylor et al. |
| 5,488,959 A | 2/1996 | Ales |
| 5,597,378 A | 1/1997 | Jervis |
| 5,667,521 A | 9/1997 | Keown |
| 5,738,667 A | 4/1998 | Solar |
| 5,762,070 A | 6/1998 | Nagamatsu |
| 5,776,079 A | 7/1998 | Cope et al. |
| 5,776,100 A | 7/1998 | Forman |
| 5,797,857 A | 8/1998 | Obitsu |
| 5,810,876 A | 9/1998 | Kelleher |
| 5,827,225 A | 10/1998 | Ma Schwab |
| 5,873,842 A | 2/1999 | Brennen et al. |
| 5,882,333 A | 3/1999 | Schaer et al. |
| 5,891,056 A | 4/1999 | Ramzipoor |
| 5,893,868 A | 4/1999 | Hanson et al. |
| 5,947,940 A * | 9/1999 | Beisel .................... 604/526 |
| 5,993,424 A | 11/1999 | Lorenzo et al. |
| 5,997,526 A | 12/1999 | Giba et al. |
| 6,007,517 A | 12/1999 | Anderson |
| 6,139,510 A | 10/2000 | Palermo |
| 6,217,567 B1 | 4/2001 | Zadno-Azizi et al. |
| 6,221,066 B1 | 4/2001 | Ferrera et al. |
| 6,248,092 B1 | 6/2001 | Miraki et al. |
| 6,254,549 B1 | 7/2001 | Ramzipoor |
| 6,254,550 B1 | 7/2001 | McNamara et al. |
| 6,290,693 B1 | 9/2001 | Jung, Jr. et al. |
| 6,306,141 B1 | 10/2001 | Jervis |
| 6,309,404 B1 | 10/2001 | Krzyzanowski |
| 6,348,041 B1 | 2/2002 | Klint |
| 6,348,045 B1 | 2/2002 | Malonek et al. |
| 6,383,146 B1 | 5/2002 | Klint |
| 6,471,697 B1 | 10/2002 | Lesh |
| 6,475,167 B1 | 11/2002 | Fleming et al. |
| 6,500,130 B2 | 12/2002 | Kinsella et al. |
| 6,502,606 B2 | 1/2003 | Klint |
| 6,517,518 B2 | 2/2003 | Nash et al. |
| 6,530,899 B1 | 3/2003 | Savage |
| 6,569,151 B1 | 5/2003 | Nash et al. |
| 6,596,963 B2 | 7/2003 | Kelly |
| 6,605,049 B1 | 8/2003 | Wagner et al. |
| 6,613,002 B1 | 9/2003 | Clark et al. |
| 6,638,372 B1 | 10/2003 | Abrams et al. |
| 6,682,608 B2 | 1/2004 | Abrams et al. |
| 6,805,676 B2 | 10/2004 | Klint |
| 6,872,192 B2 | 3/2005 | Nash et al. |
| 7,074,197 B2 | 7/2006 | Reynolds et al. |
| 7,076,285 B2 | 7/2006 | Windheuser et al. |
| 7,229,431 B2 | 6/2007 | Houser et al. |
| 7,527,606 B2 | 5/2009 | Oepen |
| 2002/0058888 A1 | 5/2002 | Biagtan et al. |
| 2002/0169457 A1 | 11/2002 | Quinn |
| 2002/0183763 A1* | 12/2002 | Callol et al. .................. 606/108 |
| 2003/0028127 A1 | 2/2003 | Balzum et al. |
| 2003/0120208 A1 | 6/2003 | Houser et al. |
| 2004/0073108 A1 | 4/2004 | Saeed et al. |
| 2004/0116957 A1 | 6/2004 | Nishide |
| 2004/0199087 A1 | 10/2004 | Swain et al. |
| 2004/0215208 A1 | 10/2004 | Foushee et al. |
| 2005/0027212 A1 | 2/2005 | Segner et al. |
| 2005/0075647 A1 | 4/2005 | Walters et al. |
| 2005/0143770 A1* | 6/2005 | Carter et al. .................. 606/170 |
| 2005/0148902 A1 | 7/2005 | Minar et al. |
| 2005/0197663 A1* | 9/2005 | Soma et al. .................... 606/108 |
| 2005/0209533 A1 | 9/2005 | Lorenz |
| 2005/0267442 A1 | 12/2005 | Von Oepen |
| 2005/0283122 A1 | 12/2005 | Nordgren |
| 2006/0020256 A1 | 1/2006 | Bell et al. |
| 2006/0100544 A1 | 5/2006 | Ayala et al. |
| 2006/0100545 A1 | 5/2006 | Ayala et al. |
| 2007/0060908 A1 | 3/2007 | Webster et al. |
| 2007/0149946 A1 | 6/2007 | Viswanathan et al. |
| 2007/0167065 A1 | 7/2007 | Melsheimer et al. |
| 2007/0185414 A1 | 8/2007 | Urbanski et al. |
| 2007/0191790 A1 | 8/2007 | Eells et al. |

FOREIGN PATENT DOCUMENTS

| | | |
|---|---|---|
| EP | 1 057 500 A1 | 12/2000 |
| WO | WO 93/14805 | 8/1993 |
| WO | WO 96/10436 | 4/1996 |
| WO | WO 99/44510 | 9/1999 |
| WO | WO 00/74565 A1 | 12/2000 |
| WO | WO 02 094364 A2 | 11/2002 |
| WO | WO 2004/033016 | 4/2004 |
| WO | WO 2004/049970 A2 | 6/2004 |
| WO | WO 2004/050161 A1 | 6/2004 |
| WO | WO 2005/011788 A1 | 2/2005 |
| WO | WO 2005/025660 A1 | 3/2005 |
| WO | WO 2005/089852 A1 | 9/2005 |
| WO | WO 2006/039216 A2 | 4/2006 |
| WO | WO 2007/084474 A1 | 7/2007 |
| WO | WO 2007/089891 A3 | 8/2007 |
| WO | WO 2007/089893 A1 | 8/2007 |

OTHER PUBLICATIONS

Notification of Transmittal of International Preliminary Report on Patentability (Jan. 10, 2008).
Office Action dated Mar. 17, 2008 U.S. Appl. No. 11/706,548 issued in related application.
Office Action dated Apr. 7, 2008 U.S. Appl. No. 11/699,174 issued in related application.
Office Action dated May 16, 2008 U.S. Appl. No. 11/763,355 issued in related application.
Office Action dated May 30, 2008 U.S. Appl. No. 11/507,805 issued in related application.
Office Action dated May 23, 2008 U.S. Appl. No. 11/652,430 issued in related application.
International Search Report—PCT/US2007/04827 & Opinion (Mar. 14, 2008).
Suppl) Notification of Transmittal of International Preliminary Report on Patentability—PCT/US2007/002743—(Jun. 3, 2008).
The Journal of Invasive Cardiology entitled "Use of a Second Buddy Wire During Percutaneous Coronary Interventions: A Simple Solution for Some Challenging Situations" dated Apr. 25, 2005, pp. 1-8.
Office Action Restriction dated Mar. 3, 2008 U.S. Appl. No. 11/507,805 issued in related application.
Office Action Restriction dated Jul. 2, 2008 U.S. Appl. No. 11/699,171 issued in related application.

(56) References Cited

OTHER PUBLICATIONS

International Search Report & Opinion—PCT/US2006/040843 (Feb. 7, 2007).
International Preliminary Report on Patentability—PCT/US007/002741 (Jun. 25, 2008).
International Search Report—PCT/US2006/040843 (Jan. 31, 2007).
International Search Report—PCT/US2007/002743 (Jun. 14, 2007).
International Search Report—PCT/US2007/002741 (Jul. 9, 2007).
International Search Report—PCT/US2006/042184 (Mar. 1, 2007.
International Search Report—PCT/US2007/001066 (Jun. 18, 2007).
International Search Report—PCT/US2007/004827 (Oct. 23, 2007).
Office Action dated Nov. 15, 2007 issued in related U.S. Appl. No. 11/652,430.
Office Action dated Oct. 20, 2008 U.S. Appl. No. 11/549,481 issued in co-pending application.
Office Action dated Oct. 28, 2008 U.S. Appl. No. 11/507,805 issued in co-pending application.
Office Action dated Nov. 20, 2008 U.S. Appl. No. 11/763,355 issued in co-pending application.
Office Action dated Nov. 21, 2008 U.S. Appl. No. 11/549,473 issued in co-pending application.
Office Action dated Nov. 21, 2008 U.S. Appl. No. 11/699,171 issued in co-pending application.
Office Action dated Dec. 11, 2008 U.S. Appl. No. 11/652,430 issued in co-pending application.
Advisory Action dated Jan. 16, 2009 U.S. Appl. No. 11/507,805 issued in co-pending application.
International Preliminary Report on Patentability and Written Opinion (Jul. 24, 2008) PCT/US2007/001066.
Office Action dated Sep. 26, 2008 U.S. Appl. No. 11/706,548 issued in related application.
Office Action dated Oct. 15, 2008 U.S. Appl. No. 11/699,174 issued in related application.
Advisory Action dated Mar. 6, 2009 U.S. Appl. No. 11/652,430 issued in co-pending application.
Office Action dated Mar. 30, 2009 U.S. Appl. No. 11/699,174 issued in co-pending application.
Office Action dated Apr. 1, 2009 U.S. Appl. No. 11/507,805 issued in co-pending application.
Office Action dated Apr. 7, 2009 U.S. Appl. No. 11/706,548 issued in co-pending application.
Office Action dated Apr. 14, 2009 U.S. Appl. No. 11/549,481 issued in co-pending application.
Office Action dated May 8, 2009 U.S. Appl. No. 11/699,171 issued in co-pending application.
Office Action dated Jun. 4, 2009 U.S. Appl. No. 11/549,473 issued in co-pending application.
Office Action dated Jun. 9, 2009 U.S. Appl. No. 11/763,355 issued in co-pending application.
Office Action dated Jun. 12, 2009 U.S. Appl. No. 11/699,174 issued in co-pending application.
Advisory Action dated Jun. 25, 2009 U.S. Appl. No. 11/549,481 issued in co-pending application.
Advisory Action dated Jun. 22, 2009 U.S. Appl. No. 11/706,548 issued in co-pending application.
Office Action dated Jun. 23, 2009 U.S. Appl. No. 11/652,430 issued in co-pending application.
Office Action dated Aug. 3, 2009 U.S. Appl. No. 11/699,174 issued in co-pending application.
Office Action dated Sep. 16, 2009 U.S. Appl. No. 11/549,481 issued in co-pending application.
Office Action dated Oct. 1, 2009 U.S. Appl. No. 11/763,355 issued in co-pending application.
Office Action dated Oct. 14, 2009 U.S. Appl. No. 11/507,805 issued in co-pending application.
Office Action dated Oct. 23, 2009 U.S. Appl. No. 11/706,548 issued in co-pending application.
Office Action dated Dec. 9, 2009 U.S. Appl. No. 11/652,430 issued in co-pending application.
Office Action dated Jan. 19, 2010 U.S. Appl. No. 11/699,171 issued in co-pending application.
Office Action dated Apr. 2, 2010 U.S. Appl. No. 11/507,805 issued in co-pending application.
Office Action dated Apr. 6, 2010 U.S. Appl. No. 11/763,355 issued in co-pending application.
Office Action dated Mar. 12, 2010 U.S. Appl. No. 11/699,174 issued in co-pending application.
Office Action dated Apr. 21, 2010 U.S. Appl. No. 11/706,548 issued in co-pending application.

* cited by examiner

WIRE GUIDE HAVING DISTAL COUPLING TIP

CROSS-REFERENCE TO RELATED APPLICATIONS

This application claims the benefit of U.S. Provisional Application Ser. No. 60/711,102, filed on Aug. 25, 2005, entitled "WIRE GUIDE HAVING DISTAL COUPLING TIP," the entire contents of which are incorporated herein by reference.

FIELD OF THE INVENTION

This invention relates generally to wire guide for use in intracorporeal procedures, and more particularly relates to the construction of a wire guide to be coupled to a previously introduced wire guide for assistance during interventional procedures in vessels with proximal tortuosity, or as a more substantial wire guide for angioplasty procedures, stenting procedures, and other device placement procedures and their related devices.

BACKGROUND OF THE INVENTION

Proximal tortuosity of the vasculature is problematic for all medical catheter devices such as atherectomy devices, angioplasty devices, stent delivery devices, and filter delivery devices. Wire guides are therefore typically used to navigate the vasculature of a patient during percutaneous interventional procedures. Once the wire guide has been introduced, it may then be used to introduce one or more medical catheter devices. Thus, most wire guides are typically 0.014 inches in diameter and have a lubricious coating to enhance wire guide introduction movement. Conventional 0.014 inch floppy wire guides must have sufficient flexibility and torque control for navigation through tortuous vessels. At the same time, the wire guide must have a certain amount of rigidity to pass through lesions, straighten extremely tortuous vessels, and support medical catheter devices that are introduced over the wire guide.

Accordingly, wire guides are subjected to potentially conflicting requirements. Conventional 0.014 inch floppy wire guides are usually sufficient for navigation of moderately tortuous vessels. However, in some situations the wire guide tip may prolapse away from the site to which it is guiding the device. For example, balloon angioplasty in vessels with proximal tortuosity has been associated with a higher incidence of acute complications and procedural failure due to the inability to cross lesions with a conventional floppy wire guide, and due to the inability of the wire guide to provide adequate support to the balloon catheter. Heavy-duty wire guides, on the other hand, are generally not well suited as primary wire guides because of their stiffness and potential for causing injury to the vessel during introduction.

It may therefore be desirable to use conventional floppy wire guides for navigation of tortuous vessels, and then enhance the conventional wire guide with a supplemental wire guide. The supplemental wire guide will straighten out the vessel curves and ease further wire guide movement. Additionally, the supplemental wire guide provides greater support and enhances the tracking of balloons, stents, stent delivery devices, atherectomy devices, and other medical catheter devices as compared to a conventional floppy wire guide. This technique is commonly referred to as the "Buddy Wire" technique, details of which are disclosed in U.S. patent application Ser. No. 11/081,146, filed Mar. 16, 2005.

However, the navigation of the supplemental wire guide parallel to the first wire guide is an exacting and time consuming process in which additional difficulties are encountered. For example, the second wire guide can cork screw or coil around the first wire guide, which may result in immobilization or unintended movement of the first wire guide, which in turn may require the retraction and re-feeding of the supplemental wire guide and/or the primary wire guide. Moreover, if retraction of the supplemental wire guide is necessary, either of the wire guides may become contaminated and the entire process may need to be restarted with sterile components. The time consumed by this process can be critical to the success of the procedure. Additionally, when traversing through the heart of a patient, and particularly the ostium, the larger open space of the heart makes identical placement of the supplemental wire guide somewhat difficult.

Accordingly, there exists a need to provide a supporting wire guide for percutaneous interventional procedures that may be easily and reliably traversed through the vasculature to a position proximate a previously introduced wire guide.

BRIEF SUMMARY OF THE INVENTION

The present invention provides a coupling wire guide for intracorporeal procedures which may be coupled to a previously introduced wire guide, thereby permitting introduction of the coupling wire guide over the previously introduced wire guide in a manner that is both reliable as well as traceable. One embodiment of the coupling wire guide includes a main body having a distal end and a tip portion connected to the distal end of the main body. The tip portion defines an axial passageway having a distal opening and a proximal opening, the passageway and openings being sized to receive the previously wire guide therein. The tip portion includes a linking member fixedly connected to the distal end of the main body to provide a secure connection between the distal end of the main body and the tip portion.

According to more detailed aspects of the invention, the linking member comprises a coil attached to the distal end of the main body. Preferably, this coil is constructed of platinum or other material that exhibits good radiopaque properties to provide an identifiable marker for tracing the coupling wire guide. In another version, the main body includes a main coil, and a distal portion of the main coil extends into the tip portion to define the linking member. The extending portion of the main coil securely links the tip portion in the main body. Additionally, the coil preferably includes a change in pitch over at least a section of the tip portion, thereby providing a detectable marker for tracking the tip portion. In a third version, the linking member comprises a bridge interconnecting first and second tubular portions. The first tubular portion is axially spaced from the second tubular portion. The first tubular portion is fixedly connected to the distal end of the main body, preferably by welding, and the second tubular portion is fixedly connected to the tip portion. This version of the linking member may be formed by cutting a sheet of material into an H-shape, and then rolling the legs of the H-shape to form the first and second tubular portions. Alternatively, this version of the linking member may be formed by laser cutting a cannula to form the desired shape.

According to still further detailed aspects of the invention, the linking member is positioned proximate the proximal opening to provide support to the tip portion adjacent the proximal opening. The tip portion is preferably constructed of a plastic material and is molded over the linking member. The tip portion may further be formed by a plastic material having radiopaque particles contained therein for providing tracking of the coupling wire guide. The axial passageway preferably extends generally parallel to the main body and may include an inner surface formed of a friction reducing material. The axial passageway may be coaxial with, or offset from, the main body. The axial passageway may further include a curved section adjacent the proximal opening, the curved section extending radially. The curved section may be formed in or as part of the distal end of the main body. The proximal opening may face axially, particularly when the axial passageway extends generally parallel to and coaxially the main body. The proximal opening may face radially, particularly when the axial passageway is coaxial with the main body.

BRIEF DESCRIPTION OF THE DRAWINGS

The accompanying drawings incorporated in and forming a part of the specification illustrate several aspects of the present invention, and together with the description serve to explain the principles of the invention. In the drawings.

DETAILED DESCRIPTION OF THE INVENTION

Figure 1:
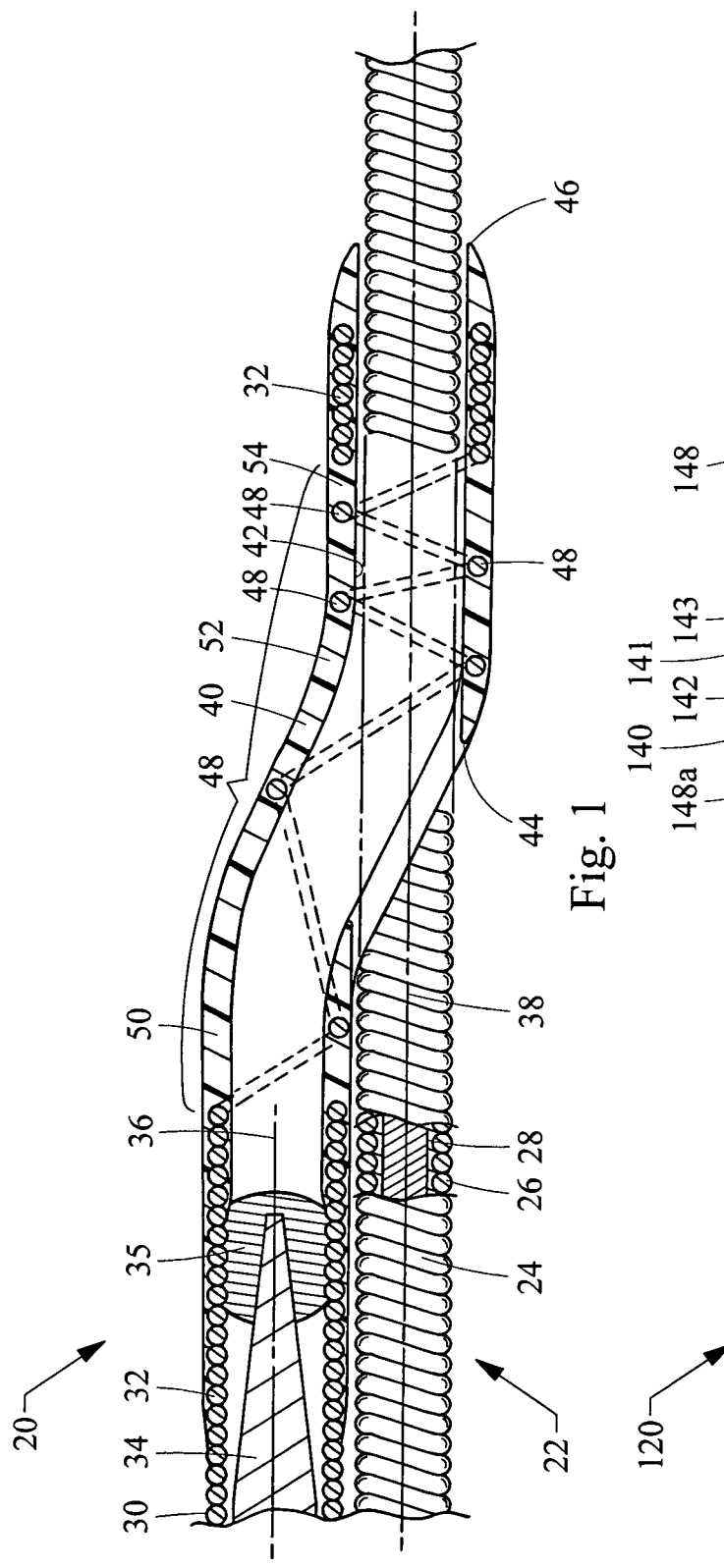
FIG. 1 is a cross-sectional view, partially cut-away, of a coupling wire guide constructed in accordance with the teachings of the present invention, shown coupled to a second previously placed wire guide.

Turning now to the figures, FIG. 1 depicts a cross-sectional view, partially cut-away, of a coupling wire guide 20 constructed in accordance with the teachings of the present invention. The coupling wire guide 20 is structured to be introduced over a previously introduced wire guide 22. While wire guides are generally used in percutaneous interventional procedures, it will be recognized by those skilled in the art that the wire guide 20 of the present invention may also be employed in endoscopic or other intracorporeal procedures.

The previously introduced wire guide 22 has been shown as comprising a main body 24 having a coil 26 disposed over a mandrel 28 and defining a longitudinal axis 38. It will be recognized that wire guide 22 may take numerous forms as many types of wire guides are known in the art, including solid wires, tubular wires, coiled wires, and combinations thereof. Similarly, the coupling wire guide 20 includes a main body 30 depicted as a coil 32 disposed over a mandrel 34 and which defines a longitudinal axis 36. The distal end of the mandrel 34 is connected to the coil 32, such as by solder 35. The main body 30 may take other forms, such as those discussed above with regard to wire guide 22. For example, the main body 30 may replace the mandrel 34 with a safety wire, and likewise may not require a coil 32 but may simply comprise the mandrel itself or some variation thereof such as a mandrel having a coil tip section, such as is shown in U.S. Pat. No. 5,243,996.

To provide simple and reliable introduction of the coupling wire guide 20, a unique tip portion 40 has been formed at the distal end of the main body 30. The tip portion 40 is formed as a tubular member so as to define an internal passageway 42. At least a portion of the internal passageway 42 extends axially and is in communication with a proximal opening 44 and a distal opening 46. As shown in FIG. 1, the proximal opening 44, passageway 42, and distal opening 46 are sized and structured to receive the previously introduced wire guide 22 therein, thereby permitting coupling of the coupling wire guide 20 to the previously introduced wire guide 22. Accordingly, coupling wire guide 20 is harnessed to the previously introduced wire guide 22 allowing the coupling wire guide 20 to simply be translated along the previously introduced wire guide 22 for substantially identical placement.

The tip section 40 is preferably constructed of plastic material, and is linked to the main body 30 of the coupling wire guide 20 by forming the plastic material of the tip 40 around the coil 32 of the coupling wire guide 20. Preferably, the plastic material of the tip portion 40 is over molded onto an extension of coil 32, which is structured as shown in FIG. 1. Specifically, the tip portion 40 includes a proximal section 50 which is attached to the coil 32 of the main body 30, a curved section 52 which extends radially away from the longitudinal axis 36, and a distal section 54 which defines the portion of the internal passageway 42 receiving the previously placed wire guide 22 as well as the distal opening 46. It can be seen that the coil 32 increases in pitch through a substantial part of the tip portion 40, the area of increased pitch being indicated by reference numeral 48. The coil 32 resumes its normal pitch at the distal section 54 of the tip portion 40. The curved section 52 of the tip portion 40 also serves to define the proximal opening 44. Because of the angle of the curved section 52, the proximal opening 44 faces both radially as well as axially, thereby permitting translation of the coupling wire guide 20 over the previously introduced wire guide 22 with minimal change in shape or deformation of the previously introduced wire guide 22.

It will be recognized by those skilled in the art that by extending the coil 32 into the tip section 40, support is provided to the tip portion 40 and its openings 44, 46 and passageway 42. At the same time, the increased pitch 48 also provides flexibility to curved section 52 and close tracking between the wire guides 20, 22. The coil 32 also serves as a safety linking member in the unlikely event that the tip section 40 would be subjected to forces or conditions which might otherwise disconnect the tip portion 40 from the main body 30. Additionally, it will be recognized that the increased pitch 48 of the coil 32 provides an identifiable marker that indicates the location of the tip section 40 of the coupling wire guide 20. In particular, the increased pitch 48 serves to identify the proximal opening 44, while the resumption of normal pitch in the coil 32 serves to identify the distal opening 46. In this manner, the introduction of the coupling wire guide 20 along the previously introduced wire guide 22 may be tracked and its location confirmed. Further, when the previously introduced wire guide 22 includes radiopaque markers, such as at its distal tip, its position relative to the openings 44, 46, and hence the coupling or decoupling of the wire guides 20, 22 can be determined.

Accordingly, it can be seen that the coupling wire guide 20 may be separately introduced to a nearly identical position by coupling the tip portion 40 to the previously introduced wire guide 22, whereby the coupling wire guide 20 need only be translated relative to the previously introduced wire guide 22 with minimal concern over the particular pathway being navigated. Likewise, the extension of the main coil 32 of the coupling wire guide 20 into the tip section 40 serves to provide numerous features, including a safety feature by securely linking the tip section 40 to the main body 30, a support feature by positioning the coil 32 proximate the openings 44, 46 while still providing sufficient flexibility to navigate tortuous vessels, and also a tracking feature by providing an identifiable marker for locating the distal tip 40 of the wire guide 20.

Figure 2:
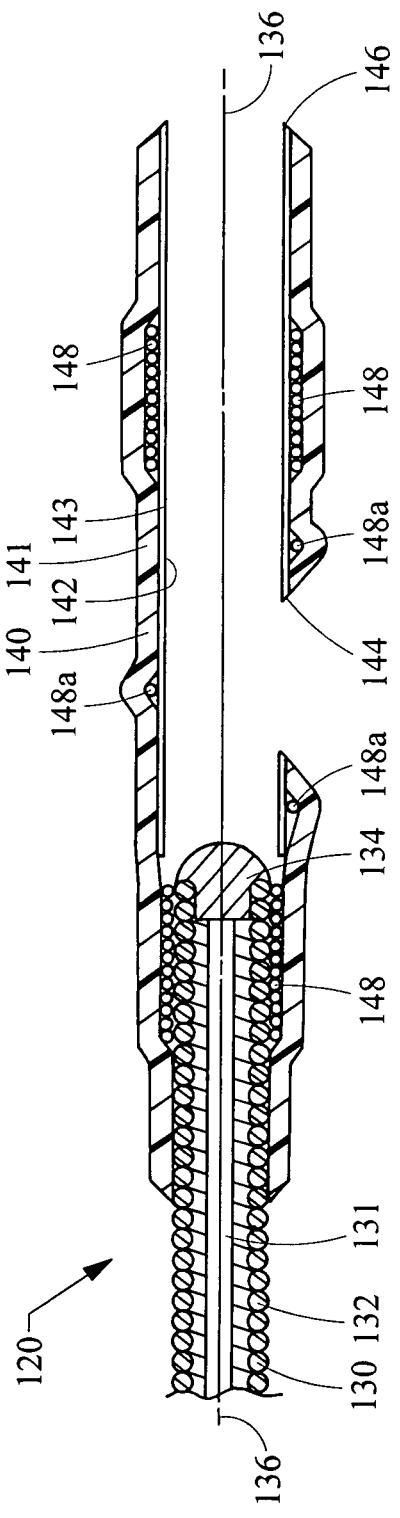
FIG. 2 is an alternate embodiment of the coupling wire guide depicted in FIG. 1 constructed in accordance with the teachings of the present invention.

An alternate embodiment of the coupling wire guide 120 has been depicted in the cross-sectional view of FIG. 2. As with the prior embodiment, the wire guide 120 generally includes a main body 130 defined by a coil 132 disposed over a mandrel 131 connected to a distal cap 134 and extending along a longitudinal axis 136, although the main body 130 may take many forms as previously discussed.

Unlike the prior embodiment which integrally used the main coil 32 as a linking member for the tip portion 40, the present embodiment utilizes a second coil 148 for the linking member that is fixedly attached to the main body 130. Preferably, the second coil 148 is formed of platinum or other material which has good radiopaque properties to provide clear tracking and location identification. The second coil 148 may be attached to the main body 130 by any suitable means, and preferably by soldering or welding to the main coil 132, although other bonding techniques, structures, or materials such as adhesives may be employed. The second coil 148 is part of a tip portion 140 constructed of an outer sleeve 141 and an inner sleeve 143 defining an internal axial passageway 142 therein. It can be seen that the internal passageway 142 is coaxial with the longitudinal axis 136 of the main body 130.

Similar to the prior embodiment, a portion of the secondary coil 148 is stretched to create a relaxed section having increased pitch identified by numeral 148a, which also improves the ability to locate and track the movement of the tip portion 140. Likewise, the increased pitch 148a serves to identify the proximal opening 144, while the resumption of normal pitch in the coil 32 serves to identify the distal opening 146. The increased pitch 148a of the coil is still sufficient to prevent excessive bending or kinking of the tip portion 140 while providing sufficient flexibility for navigation With the secondary coil 148 structured as shown in FIG. 2, the outer sleeve 141 may be formed around the secondary coil 148 and distal end of the main body 130, preferably by forming the sleeve 141 of a heat shrinkable plastic and shrinking the outer sleeve 141, although other plastics and forming techniques may be employed, such as injection molding. The inner sleeve 143 is preferably formed of a low friction material such as PTFE to provide easy translation of the previously placed wire guide within the internal passageway 142. The tip portion 140 is cut or otherwise shaped to define a proximal opening 144 which faces radially, and is located between two adjacent windings of the relaxed section 148a of the secondary coil 148. The most distal end of the tip portion 140 defines the distal opening 146 through which the previously placed wire guide passes. By forming the linking member out of a second coil 148, the material of the coil 148 can be selected for certain properties such as radiopacity, stiffness, size, etc., while achieving all of the aforementioned benefits of the invention.

Figure 3:
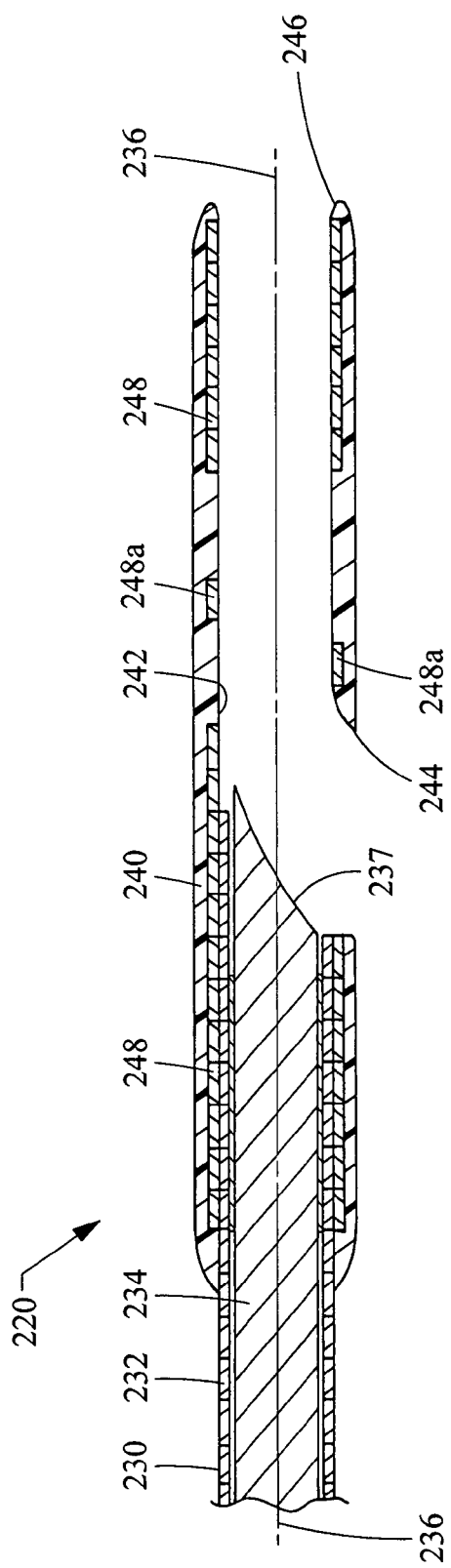
FIG. 3 is another alternate embodiment of the coupling wire guide depicted in FIG. 1 constructed in accordance with the teachings of the present invention.

Turning now to FIG. 3, yet another embodiment of a coupling wire guide 220 has been depicted in accordance with the teachings of the present invention. In this embodiment, the main body 230 of the wire guide 220 has been shown as having a flat wire coil 232 disposed over a mandrel 234 and defining a longitudinal axis 236. A tip portion 240 includes a secondary coil 248 which is also constructed of a flat wire that is attached to the coil 232 of the main body 230 by any of the methods previously mentioned. The secondary coil 248 is stretched to define a relaxed section having windings of an increased pitch, identified by numeral 248a, over which a plastic material is molded to define the tip portion 240 and an axial passageway 242, the axial passageway 242 being in communication with a proximal opening 244 and a distal opening 246. The coil 248 and its increased pitch thus serves to radiographically identify the location of the openings 244, 246, as in the prior embodiments. The coil 248 extends around the proximal opening 244 to provide support thereto. As illustrated in this embodiment, the distal end of the mandrel 234 includes a curved surface 237 positioned adjacent the proximal opening 244. The curved surface 237 facilitates placement of the coupling wire guide over a previously introduced wire guide. The mandrel 234 of the main body 230 and wire guide 220 serve to assist in the translation of the wire guide 220 along a previously placed wire guide.

Figure 4:
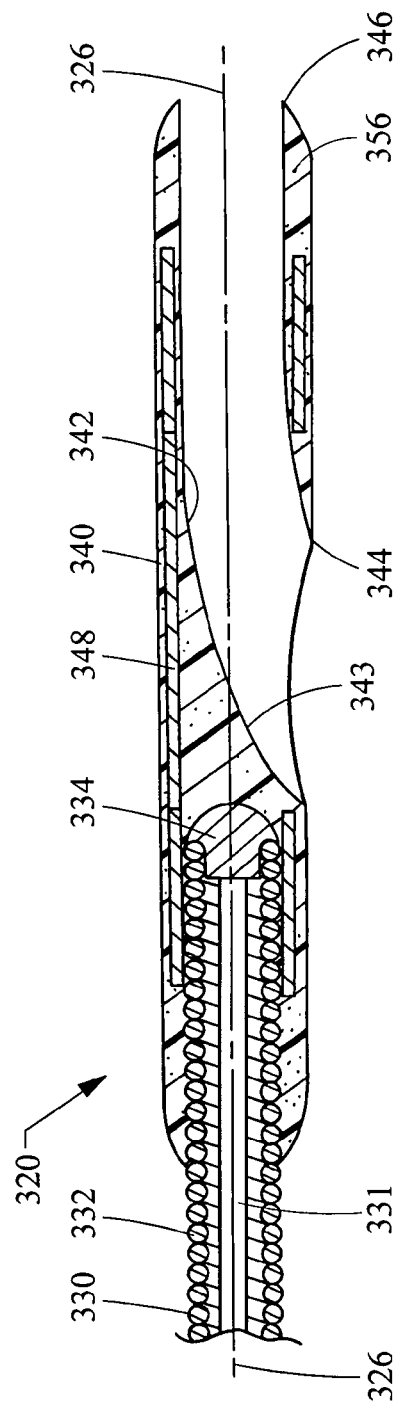
FIG. 4 is yet another alternate embodiment of the coupling wire guide depicted in FIG. 1 constructed in accordance with the teachings of the present invention.
Figure 5:
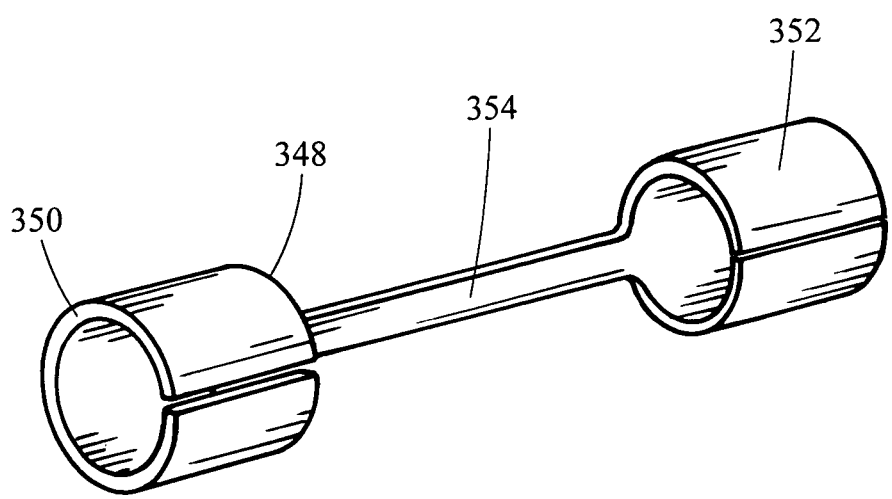
FIG. 5 is a perspective view of the linking member forming a portion of the coupling wire guide depicted in FIG. 4.

Still yet another embodiment of a coupling wire guide 320 is depicted in FIG. 4 in accordance with the teachings of the present invention. As with the prior embodiments, the wire guide 320 includes a main body 330 including a coil 320 disposed over a mandrel 331 connected to a distal cap 334, and defining a longitudinal axis 326. The wire guide 320 includes a tip section 340 employing an alternative linking member 348, which has been separately depicted in the perspective view of FIG. 5. The linking member 348 generally includes a first tubular portion 350 connected to a second tubular portion 352 by way of a bridge portion 354. By way of example, the linking member 348 may be formed by cutting a sheet of material such as Nitinol or stainless steel into an H-shape, and then rolling the legs of H-shape to form the tubular portions 350 and 352. It will also be recognized by those skilled in the art that the linking member 348 may be formed by many different methods known in the art, such as laser cutting a cannula or machining any other tubular member to form the desired shape.

Turning back to FIG. 4, the linking member 348, and particularly the first tubular portion 350, is securely and fixedly attached to the distal end of the main body 330, preferably by welding or other known techniques. The bridge portion 354 provides support to the plastic material of the tip portion 340 in the area adjacent the proximal opening 344 to prevent kinking or excessive bending, while providing sufficient flexibility for navigation. Preferably, the tip portion 340 is formed by injection molding a plastic material around the distal end of the main body 330 and linking member 348 to define an internal passageway 342 connected to and in communication with the proximal opening 344 and distal opening 346. It will also be recognized that the axial passageway 342 is formed with a curved portion 343 which extends radially towards the proximal opening 344. The curved portion 343 assists with smooth translation of the wire guide 320 over the previously introduced wire guide 322.

Similar to the prior embodiments, the different size and shape of the bridge portion 354 relative to the tubular portion 352 serves to identify the location of openings 344, 346. However, it will be recognized by those skilled in the art that the material of the tip portion 340 may further include radiopaque particles 356 or other detectable particles, which may likewise be concentrated in the regions of the proximal and distal opening 344, 346. It will also be recognized that such radiopaque particles may be employed in any of the embodiment previously described. While the linking member 348 itself provides an identifiable marker, the use of radiopaque particles 356 further assists the tracing and locating of the wire guide 320 and its tip portion 340.

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. A coupling wire guide for intracorporeal procedures, the coupling wire guide comprising:
   a main body having a distal end;
   a tip portion connected to the distal end of the main body, the tip portion defining an axial passageway having a distal opening and a proximal opening, the axial passageway sized to receive a second wire guide therein; and
   a linking member non-rotatably connected to the distal end of the main body, the tip portion constructed of a plastic material and formed over the linking member, the linking member including a coil attached to the distal end of the main body, wherein the coil increases in pitch to define a space between adjacent loops of the coil, the space sized and positioned to correspond to the proximal opening of the axial passageway, and wherein the coil decreases in pitch at a location distally beyond the proximal opening.

2. The coupling wire guide of claim 1, wherein the main body includes a main coil, and wherein the coil is welded to the main coil.

3. The coupling wire guide of claim 1, wherein the main body includes a main coil, and wherein a distal portion of the main coil extends into the tip portion to define the coil of the linking member.

4. The coupling wire guide of claim 1, wherein the coil extends distally to a location proximate the distal opening.

5. The coupling wire guide of claim 1, wherein the linking member is positioned proximate the proximal opening to provide support to the tip portion adjacent the proximal opening.

6. The coupling wire guide of claim 1, wherein the plastic material is formed as a tubular member and includes an aperture corresponding to the proximal opening.

7. The coupling wire guide of claim 1, wherein the axial passageway extends generally parallel to the main body, but is not co-axial with the main body.

8. The coupling wire guide of claim 7, wherein the proximal opening faces axially.

9. The coupling wire guide of claim 1, wherein the proximal opening faces axially.

10. The coupling wire guide of claim 1, wherein the proximal opening faces radially.

11. The coupling wire guide of claim 1, wherein the axial passageway includes an inner surface formed of a friction reducing material.

12. The coupling wire guide of claim 1, wherein the axial passageway includes a curved section adjacent the proximal opening, the axial passageway following a curved path in the curved section and extending radially.

13. The coupling wire guide of claim 12, wherein the curved section is formed by the distal end of the main body.

14. The coupling wire guide of claim 1, wherein plastic material includes radiopaque particles contained therein.

15. The coupling wire guide of claim 1, wherein the coil and tip portion together define the axial passageway.

16. The coupling wire guide of claim 1, wherein the main body defines a closed distal end surface that is exposed to the axial passageway and the proximal opening for guiding the previously introduced wire guide.

17. The coupling wire guide of claim 1, wherein the distal end of the main body includes a distal cap defining a closed distal end surface.

18. The coupling wire guide of claim 1, wherein the main body is elongated and has a length substantially greater than the tip portion.

19. The coupling wire guide of claim 1, wherein the plastic material of the tip portion is directly connected to the main body.

20. The coupling wire guide of claim 1, wherein the linking member is axially coextensive with the tip portion.

21. A coupling wire guide for intracorporeal procedures, the wire guide comprising:
   a main body having a distal end;
   a linking member rigidly connected to the distal end of the main body, wherein the linking member comprises a non-tubular bridge portion interconnecting a first tubular portion and a second tubular portion, the first tubular portion axially spaced from the second tubular portion, the first tubular portion fixedly connected to the distal end of the main body; and
   a plastic material encapsulating the linking member and distal end to define a tip portion, the tip portion defining an axial passageway having a distal opening and a proximal opening, the axial passageway sized to receive a second wire guide therein.

22. The coupling wire guide of claim 21, wherein the linking member provides an identifiable marker for radiographic tracing.

23. The coupling wire guide of claim 21, wherein the plastic material includes radiopaque particles contained therein.

24. The coupling wire guide of claim 21, wherein the linking member extends from a location proximate the proximal opening to a location proximate the distal opening.

25. The coupling wire guide of claim 21, wherein the linking member is non-rotatably connected to the distal end of the main body.

26. The coupling wire guide of claim 21, wherein the distal end of the main body includes a distal cap defining a closed distal end surface, and wherein the closed distal end surface is exposed to the axial passageway and the proximal opening for guiding the previously introduced wire guide.

27. The coupling wire guide of claim 26, wherein the distal cap is located at an axial location aligned with, or proximal to, the proximal opening.

28. The coupling wire guide of claim 21, wherein the linking member is unitarily formed as a single piece.

* * * * *